(12) United States Patent
Raval et al.

(10) Patent No.: US 12,743,967 B1
(45) Date of Patent: Sep. 22, 2026

(54) AUDIO/VIDEO TRAINING SYSTEM FOR HEALTHCARE TRAINING

(71) Applicant: EDUCATION MANAGEMENT SOLUTIONS, LLC, Wayne, PA (US)

(72) Inventors: Sejal Raval, Coppell, TX (US); Senthamarai Kannan Ayyakkannu, Dowingtown, PA (US); Mark Jarvis, Garnet Valley, PA (US)

(73) Assignee: Education Management Solutions, LLC, Wayne, PA (US)

( * ) Notice: Subject to any disclaimer, the term of this patent is extended or adjusted under 35 U.S.C. 154(b) by 2 days.

(21) Appl. No.: 18/955,238

(22) Filed: Nov. 21, 2024

Related U.S. Application Data

(60) Provisional application No. 63/602,237, filed on Nov. 22, 2023.

(51) Int. Cl.

| | |
|---|---|
| ***G09B 23/30*** | (2006.01) |
| ***G09B 9/00*** | (2006.01) |
| ***G16H 40/67*** | (2018.01) |

(52) U.S. Cl.
CPC ............... *G09B 23/30* (2013.01); *G09B 9/00* (2013.01); *G16H 40/67* (2018.01)

(58) Field of Classification Search
CPC ........ G09B 23/26; G09B 23/28; G09B 23/30; G09B 9/00; G16H 40/67
See application file for complete search history.

(56) References Cited

U.S. PATENT DOCUMENTS

| | | | | |
|---|---|---|---|---|
| 2015/0004571 | A1* | 1/2015 | Ironside | G09B 7/073 434/185 |
| 2015/0187231 | A1* | 7/2015 | Stephanian | H04N 5/77 280/47.35 |
| 2022/0217551 | A1* | 7/2022 | Eskildsen | H04L 12/10 |

* cited by examiner

*Primary Examiner* — Timothy A Musselman
(74) *Attorney, Agent, or Firm* — Rosenberg, Klein & Lee

(57) ABSTRACT

Systems and Methods of an audio/visual healthcare training system provides remotely located medical personnel with a view of a patient simulator and physiologic patient simulator data in real time during a training session. A screen capture unit is coupled to the patient monitor for recording and display of the patient simulator physiologic data being received during the particular medical procedure being applied to the patient simulator. The patient simulator physiologic data is transmitted to a primary remote processor. A panning-zoom camera for transmitting a video of the patient simulator. Additional secondary cameras transmit videos of the patient simulator from different angles. A remote processor receives physiologic data and video of the patient simulator during the training session. A remote data storage system receives the training session data and video from the primary camera unit and/or a remote processor for saving various physiologic data.

19 Claims, 8 Drawing Sheets

38

AUDIO/VIDEO TRAINING SYSTEM FOR HEALTHCARE TRAINING

FIELD OF THE INVENTION

This invention is directed to the field of providing healthcare training systems and methods to be used in conjunction with a patient simulator for capturing and dispensing audio/visual data associated with a specific medical procedure being applied to the patient simulator.

This invention relates to a healthcare system for training medical personnel as to procedures being applied to the patient simulator for a particular medical procedure during a training session.

This invention is directed to an audio/visual healthcare training system where remotely located medical personnel are provided with a view of the patient simulator and the physiologic patient simulator data in real time during the training session.

This invention is directed to a system where a screen capture unit is coupled to the patient monitor for recording and displaying the patient simulator physiologic data being received during the particular medical procedure being applied to the patient simulator.

In particular this invention relates to an audio/video system for providing a primary camera unit wired or wirelessly receives the patient simulator physiologic data and transmits the patient simulator physiologic data to a primary remote processor.

More in particular, this invention is directed to an audio/video training system where during the training session the primary camera unit which includes a panning-zoom camera transmits patient simulator physiologic data and video of the patient simulator to a remote processor Still further this invention is directed to an audio/video training system where the remote processor receives physiologic data and a visual picture of the patient simulator during the training session.

This invention relates to an audio/video training healthcare system where the primary camera unit both receives/transmits audio/visual data from the remote processor and is adapted to receive both visual and audio data to a series of secondary remote camera units under control of the remote processor.

Still further this invention is directed to an audio/video system which includes a remote data storage system for receiving training session data from the primary camera unit and/or a remote processor for saving various physiologic data.

BACKGROUND OF THE INVENTION

In the process of training healthcare professionals, there is an increasing focus on training healthcare professionals utilizing patient simulators to demonstrate various scenarios requiring medical training. This training is most beneficial when the scenario for a particular medical procedure is repeatable or similarly when a medical procedure has a high degree of surgical difficulty. Thus it has been found that the use of patient simulators have been of great use when a patient simulator is used during training sessions of medical personnel.

Patient simulators are commercially available in many varieties such as adult, pediatric and neonatal simulators. There are full body simulators and specific task trainers that are models that represent a part or region of the human body. Patient simulators fall into two main classes of simulators, High Fidelity Simulators and Low Fidelity Simulators. Low Fidelity Simulators are simple non-programmable simulators that are used to demonstrate basic healthcare tasks. High Fidelity Simulators accept input of certain data parameters to demonstrate a broad range of scenarios where the simulator mimics human body functions during the training session.

Medical training sessions utilizing patient simulators are used in medical educational facilities. The typical environment for the medical training session is in a large demonstration room with multiple stations with each having a patient simulator and associated medical tools and instruments for the training session. In general, each simulator is operated by a single instructor for guiding the student or assessing the proficiency of the student.

The patient simulator may be used in two ways. First, the system may be used as an instruction system where the students are viewing the techniques being demonstrated by an instructor. Second, a student attends the patient simulator training session to gain experience working with a patient exhibiting different symptoms in a given scenario.

In an effort to approximate real world situations, there is the desire to provide specialized training to students in real world locations, such as a small private emergency room or the back of an ambulance. In these locations, the physical space available is very limited, and is only conducive for demonstrations to a very limited number of students.

There is also the desire to record each session in appropriate detail to assist the student during a post analysis and debriefing session.

Thus, there is a need to provide training to a large number of medical personnel or students with demonstrations of training scenarios in locations with limited space.

Additionally there is the need to provide an interactive training scenario where a patient simulator data and/or audio/video can be transmitted/received to and from a plurality of remotely located medical personnel or students.

SUMMARY OF THE INVENTION

The audio/visual training system comprises a patient simulator connected to a patient monitor. The patient monitor receives and displays patient physiological data.

The audio/visual training system has a primary camera unit has a camera unit housing and a camera unit router mounted within the camera unit housing. A pan-tilt-zoom (PTZ) camera is mounted within the camera unit housing. The PTZ camera captures a video image of the patient simulator.

The audio/visual training system has a screen capture unit coupled to the patient monitor and has a screen capture unit router. The screen capture unit is in communication with the patient monitor for capturing a physiological data video of the physiological data displayed on the patient monitor. The physiological data video is routed to the primary camera unit.

The audio/visual training system has a primary remote processor is in communication with the patient simulator and has a remote processor router for receiving the physiological data video and the video image of the patient simulator from the primary camera unit. A display screen is connected to the primary remote processor for displaying the physiological data video and the video image of the patient simulator.

The audio/visual training system has a data storage unit is coupled to the primary remote processor for storing the physiological data, the video image of the patient simulator and said physiological data video.

The primary remote processor of the audio/video training system is in communication with the patient simulator through the primary camera unit for controlling physical parameters of the patient simulator responsive to the patient physiological data transmitted by the primary remote processor.

The audio/video training system may further include a plurality of secondary camera units. Each of the plurality of secondary camera units are in communication with the primary camera unit.

Each of the plurality of secondary camera units of the audio/video training system includes a secondary camera unit housing, and a secondary PTZ camera mounted in each of the secondary camera unit housings.

Each of the secondary camera units of the audio/video training system transmits independently secondary video images of said patient simulator.

The data storage unit of the audio/video training system may be a cloud based storage unit for receiving the physiological data video and the video image of the patient simulator from the primary remote processor.

In addition to providing firsthand instruction, the system provides the ability to analyze the training session afterward in a debriefing session using the recorded session. This allows instructors and students the ability to assess the session and review critical moments during the session.

The system also provides for oversite of the training sessions through monitoring of the system components, data input and data output.

The system also provides for reconfiguration of the system as required. The reconfiguration may be made through a connection from a remote location or physically relocating a component of the system.

The audio/video training system may be implemented in a multi-tiered network permitting expansion of the training system to include multiple physical locations with control of each training location from specialized operation stations.

It is an object of the subject training system to provide audio/visual data of a patient simulator and physiologic simulator data undergoing a surgical procedure to remote locations.

It is a further object of the subject training system to provide a compact/efficient transmission of simulator physiologic parameters experienced during a simulated medical procedure.

It is a still further object of the subject training system to provide feedback from a plurality of locations to a remote processor which is adapted to control differing scenarios of a particular medical procedure.

DESCRIPTION OF THE PREFERRED EMBODIMENTS

Figure 1:
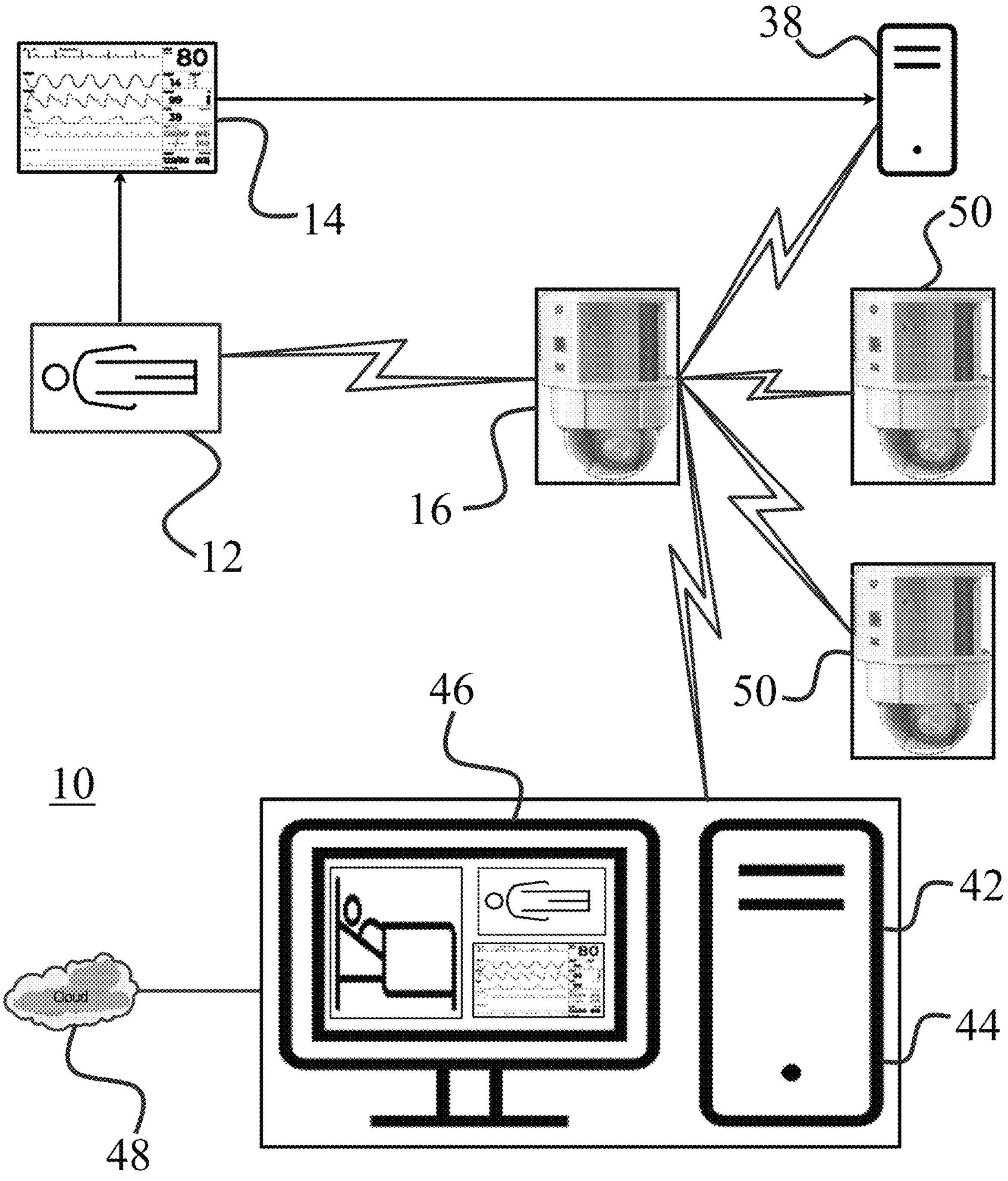
FIG. 1 is a depiction of an audio/video training system.

Referring now to FIG. 1, there is shown audio/video training system 10 for training healthcare students and professionals. System 10 utilizes a patient simulator 12 for accepting tactile manipulation associated with a particular training exercise for experiencing differing surgical or other medical procedures being applied to patient simulator 12 which as will be described in following paragraphs is audibly and/or video transmitted to a remote processor 42.

The patient simulator 12 is a specialized mannequin with the ability to simulate physiologic responses with the patient simulator 12 being controlled by a simulator processor (not shown) through the use of physiologic data parameters.

The patient simulator or human patient simulator 12 may be a life-like mannequin represented in FIG. 1, which is a life-like mannequin designed for reaction physiologically as if the patent simulator 12 were a real-life or actual patient. Such simulators 12 are well known in the art and include high fidelity patient simulators, nursing simulators, OB simulators, surgical simulators, or pediatric simulators. The overall object of the human patient simulator 12 is provided to replicate normal and abnormal bodily responses for educational/training purposes.

Examples of patient simulator 12 may include high-fidelity mannequins that register a plurality of vital signs used in surgical procedures such as Adult SimMan 3G fabricated by Laerdal Medical AS, a corporation of Norway, which is a full-body mannequin. A range of advanced patient simulators 12, which are adaptable to be used by the subject audio/video training system 10, are fabricated by Elevate Healthcare, INC., a corporation of Delaware located in Sarasota, Florida, which provides for a range of advanced patient simulators ranging from pediatric simulators to OB maternal simulators as well as surgery simulators.

The patient simulator 12, as seen in FIG. 1, is either hard wired or wirelessly connected to a patient monitor 14. The patient monitor 14 receives the physiologic data and formats the data to be displayed on a monitor screen. The physiologic data is displayed as vital signs of the patient and can include the pulse rate, respiration rate, temperature, oxygen saturation (SpO2), carbon dioxide (CO2), blood pressure, and electrocardiography (ECG) readings. Such screen monitors are well known in the art, for example maybe the Philips IntelliVue MX700 bedside patient monitor providing a real-time view of the vital signs of patients simulator 12 or some like patient monitor 14.

Figure 2:
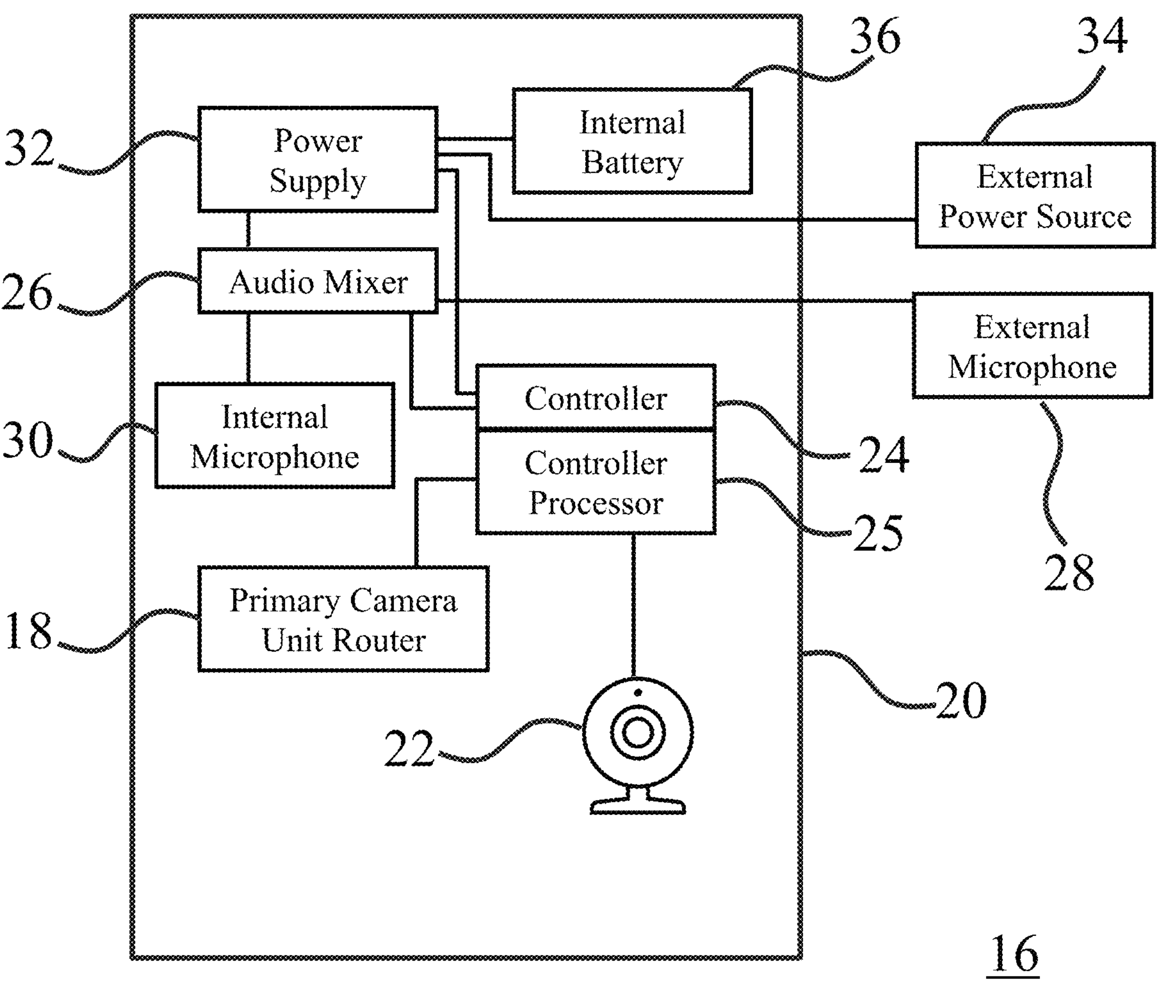
FIG. 2 shows a primary camera unit of a preferred embodiment.

The audio/video training system 10, as shown in FIG. 1, includes a primary camera unit 16. In this embodiment, the primary camera unit 16, as shown in FIG. 2, has a primary camera unit router 18 as a main wireless hub which is coupled wirelessly or hard-wired to patient simulator 12 for routing physiologic data to the patient simulator 12 in the embodiment shown in FIG. 1. The primary camera unit router 18 is wirelessly or hard-wired to a screen capture unit 38, and a plurality of secondary camera unit 50, as well as remote processor 42.

As shown in FIG. 2, the primary camera unit 16 has a camera unit housing 20 encompassing a power supply 32 and an audio mixer 26 for balancing the audio of external microphones 28 or internal microphones 30. The primary camera unit router 18 is mounted within the camera unit housing 20 and is adapted to receive/transmit signals of audio/video data received from a pan-tilt-zoom (PTZ) camera 22 mounted within the camera unit housing 20. The PTZ camera 22 permits tilting of the camera, as well as allowing rotation of the camera and lens magnification of the image as received by the camera 22. PTZ cameras are well known in the art as represented by AXIS M5526-E PTZ Camera by AXIS Communications. The AXIS camera provides output using H.264 (MPEG-4Part10/AVC) and H.265 (MPEG-HPart2/HEVC) including video streaming. The AXIS camera also provides for audio input from an external microphone as well as audio output. The PTZ camera 22 captures a video image of the patient simulator 12, instructors, and/or students while interacting with the patient simulator 12. The images from the audio and video from the primary camera unit 16 is transmitted to the remote processor 42 as seen in FIG. 1.

In addition to the PTZ camera 22 and primary camera unit router 18, the primary camera unit 16 includes a controller 24 for the PTZ camera 22 which includes a controller processor 25 for providing commands to the PTZ camera 22 for providing instructions to the PTZ camera 22 in the operation for the operations of panning, tilting, and zooming actions taken by the PTZ camera 22 during a training session. The audio mixer 26 is electrically connected to external microphones 28 or internal microphones 30. The power supply 32 is electrically connected to an external power source 34 or an internal battery 36. The external power source 34 may be a standard electrical supply or Power over Ethernet (PoE). An exemplary internal battery 36 is MimoTik POE Battery Power Pack 4-in-1 High Capacity 94.5 Wh 802.3af/at by Mimo Tik Inc.

When a command is given to the primary camera unit 16, the controller 24 receives command instructions which are transmitted to the PTZ camera 22 which performs a corresponding action to be taken by the PTZ camera 22. Thus, when the controller 24 receives a command to pan, tilt or zoom the PTZ camera 22, the PTZ camera 22 performs the corresponding action. The controller 24 may further receive a command to activate/deactivate the PTZ camera 22 operation as well as the microphones 28/30.

As seen in FIG. 1, secondary camera units 50 are connected to the primary camera unit 16 for receiving commands from the remote processor 42 through the primary camera unit 16 and transmitting audio/video files to the remote processor 42 through the primary camera unit 16. Secondary camera units 50 are used to view the training session from differing angles. This allows one camera to be a general view of the area, one camera to be zoomed in on the patient simulator 12, one camera to be zoomed in on an instrument tray, and one camera to be zoomed in on the attending physician/student.

Figure 3:
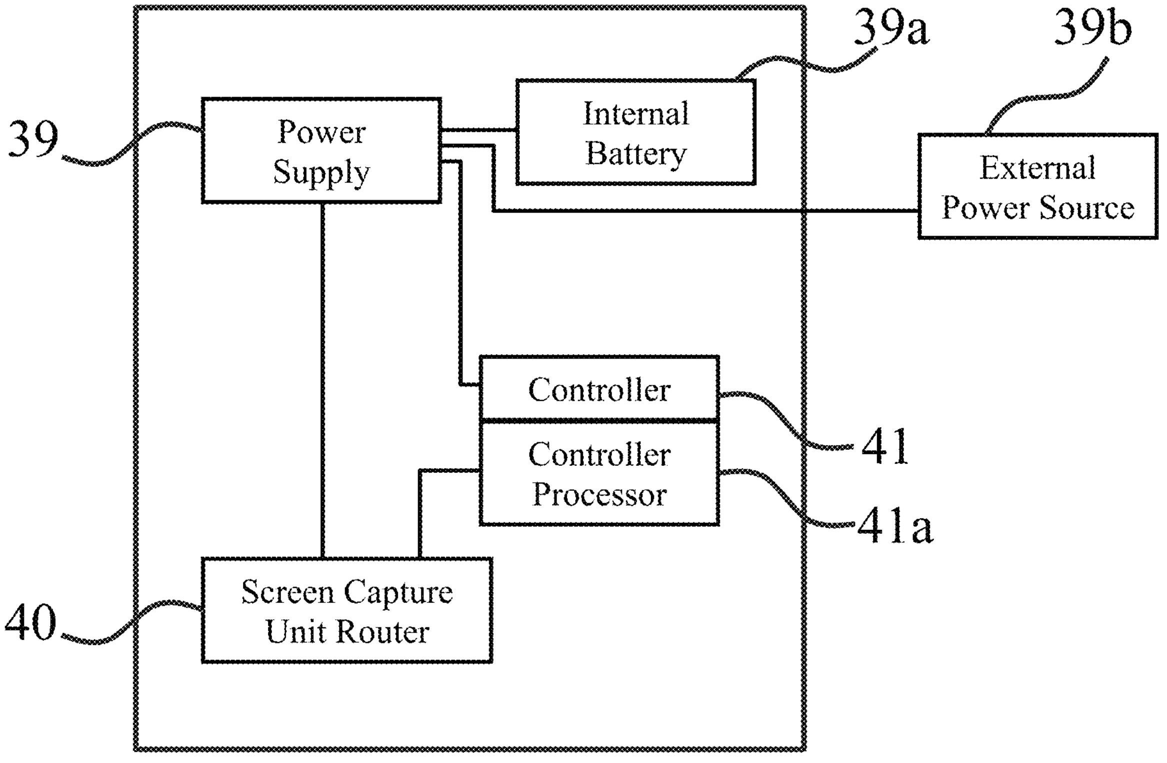
FIG. 3 shows a screen capture unit of a preferred embodiment.

As seen in FIG. 1, a screen capture unit 38 is coupled to the patient monitor 14. This connection can be a wired or wireless connection transmitting a video signal of the patient monitor 14. The screen capture unit 38 converts the video signal to a video file format for storage in a remote or contained computer system (not important to the subject matter of the invention with the exception that such video signal is maintained by a standard computer storage medium). The screen capture unit 38 captures each video frame from the video signal and converting each video frame into sequenced frames of a video file. Each frame of the video contains the image as displayed on the patient monitor 14. As seen in FIG. 3, the screen capture unit 38 includes a screen capture unit router 40 for routing the video frames to the primary camera unit 16. The screen capture unit router 40 provides a wireless or wired connection to other devices in the training system 10, such as the primary camera unit 16, as remote processor 42. Through this wired or wireless connection, the screen capture unit 38 transmits the video file containing the physiological data displayed on said patient monitor 14 to the remote processor 42 as a single file, segments of the training session, or live streaming of the training session. An exemplary screen capture unit 38 converts standard HDMI input up to 4096×2160 60 fps video with output to standard streaming protocols up to 16 Mbps, with support for H.264 (MPEG-4Part10/AVC) and H.265 (MPEG-HPart2/HEVC) video encoding.

As shown in FIG. 3, the screen capture unit 38, has a power supply 39 which may route power from an internal battery 39*a* or an external power source 39*b*. The screen capture unit 38 has a controller 41 with a controller processor 41*a* for processing the images from the patient monitor 14. All communication to and from the screen capture unit is processed through the screen capture unit router 40.

The primary remote processor 42 is in communication with the patient simulator 12 for sending the physiologic data for the patient simulator 12 to simulate some medical procedure being applied to the patient simulator 12. The primary remote processor 42 has a remote processor display screen 46, and a remote processor router 44 for receiving the physiological data video which is passed through the primary camera unit 16 from the screen capture unit 38. The remote processor router 44 of the primary remote processor 42 also receives the video image of the patient simulator 12 from the primary camera unit 16.

The remote processor display screen 46 is connected to the primary remote processor 42 for displaying the physiological data video from the patient monitor 14 via the screen capture unit 38 and the video image of the patient simulator 12 from the primary camera unit 16 and secondary camera units 50.

A data storage unit 48 is coupled to the primary remote processor 42 for storing the physiological data used for the patient simulator 12, the video images of the patient simulator 12 via the primary camera unit 16 and the secondary camera units 50 and the physiological data video of the patient monitor 14 via the screen capture unit 38. The data storage unit 48 shown in FIG. 1 is a cloud server, and may be other mass storage devices known in the art on location or remote to the audio/video learning system 10.

Figure 4:
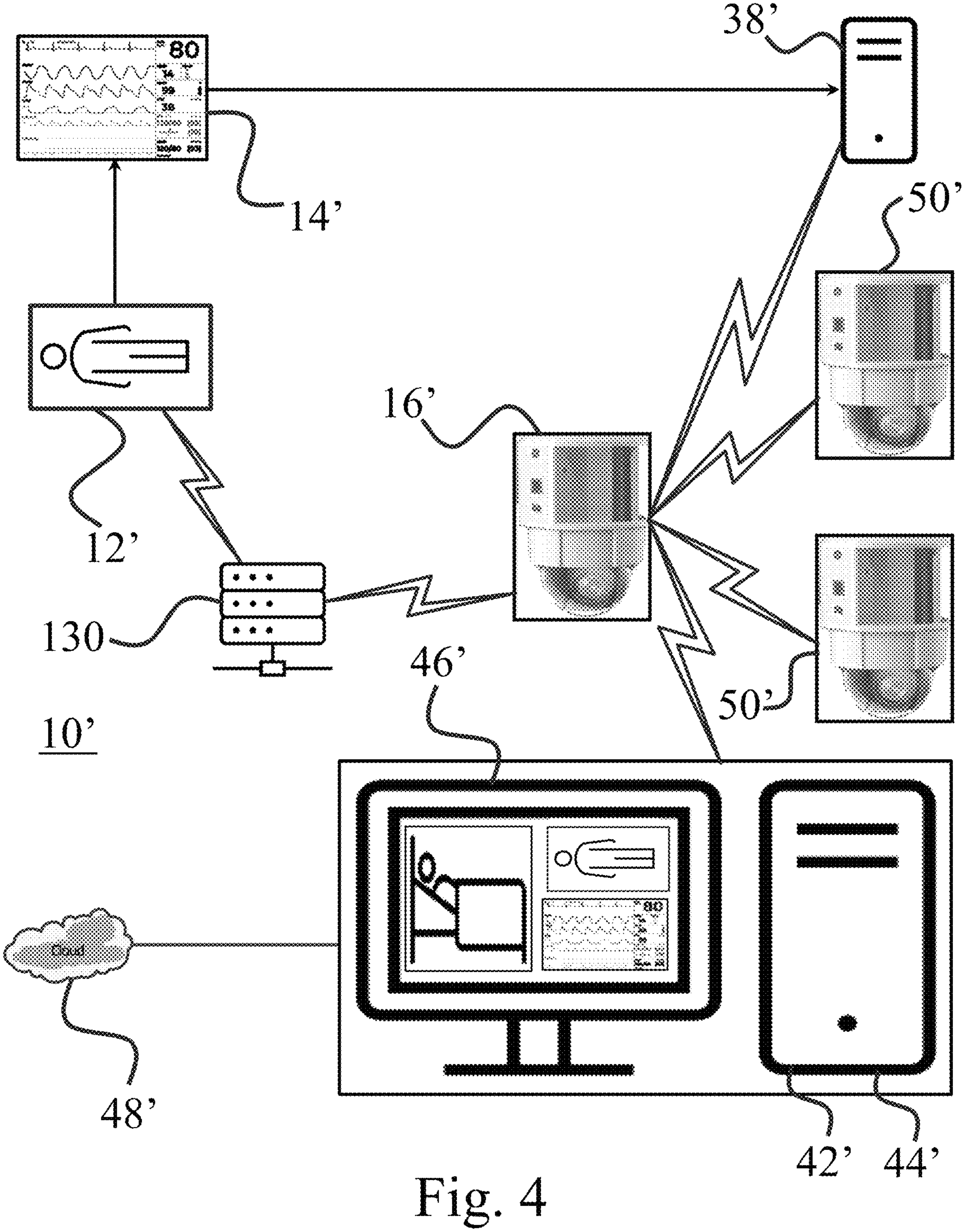
FIG. 4 is a depiction of a second embodiment of an audio/video training system.

Referring now to FIG. 4, there is shown a further embodiment of the audio/video training system 10' for training healthcare students and professionals. System 10' utilizes a patient simulator 12'. The patient simulator 12', like in other embodiments, accepts input of physiologic data parameters associated with a variety of surgical or other medical procedures and simulates these parameters as physiological conditions. The patient simulator 12' is also capable of receiving tactile manipulation by an instructor or student during a particular training exercise for demonstrating or experiencing specific scenarios being applied to patient simulator 12'. Such interactions, as will be described in following paragraphs, is audibly and/or video transmitted to a remote processor 42'.

The patient simulator 12' is a specialized teaching simulated patient in the form of a human body or body part with the ability to simulate physiologic responses with the patient simulator 12' being controlled by a simulator processor (not shown) through the use of physiologic data parameters.

The patient simulator or human patient simulator 12' maybe an artificial body represented in FIG. 4, which is a simulated life-like patient designed for providing physical autonomic reactions as if the patent simulator 12' were a real-life or actual patient. Such simulators 12' are well known in the art to provide training for numerous scenarios in various medical fields. The overall object of the human patient simulator 12' is to simulate normal and abnormal bodily responses for educational/training purposes.

Models of patient simulator 12' may include high-fidelity mannequins that duplicate a plurality of vital signs used in surgical procedures such as Adult SimMan 3G manufactured by Laerdal Medical AS, a corporation of Norway, which is a full-body mannequin. The subject audio/video training system 10' may utilize a variety of advanced patient simulators 12' produced by Elevate Healthcare, INC., a corporation of Delaware located in Sarasota, Florida.

The patient simulator 12', as seen in FIG. 4, is either hard wired or wirelessly connected to a local server 130. The local server 130 is in communication with the patient simulator 12' for sending physiologic data for the patient simulator 12' to simulate a selected medical procedure being applied to the patient simulator 12' dependent upon a surgical or medical procedure at the discretion of a training personnel.

The patient simulator 12', as seen in FIG. 4, is either hard wired or wirelessly connected to a patient monitor 14'. The patent simulator 12' sends the physiologic data to the patient monitor 14'. The patient monitor 14' receives the physiologic data and formats the data to be displayed on a monitor screen of the patient monitor 14' as graphs of unit value vs. time and instantaneous value. The physiologic data is displayed as vital signs of the patient and can include the pulse rate, respiration rate, temperature, oxygen saturation (SpO2), carbon dioxide (CO2), blood pressure, and electrocardiography (ECG) readings. Such screen monitors are well known in the art. An exemplary patient monitor is the Philips IntelliVue MX700 bedside patient monitor providing a real-time view of the vital signs of patients simulator 12'.

As shown in FIG. 4, the audio/video training system 10' includes a primary camera unit 16' and multiple secondary camera units 50'. In this embodiment, the primary camera unit 16' incorporates a primary camera unit router 18'. The primary camera unit router 18' is a main wireless hub which is coupled wirelessly or hard-wired to patient simulator 12 through the local server 130. Physiologic data is sent to the patient simulator 12' from the local server 130 or a remote processor 42'. The primary camera unit router 18' is also wirelessly or hard-wired to a screen capture unit 38', and a plurality of secondary camera unit 50', as well as remote processor 42'.

The primary camera unit 16' is analogous to the primary camera unit 16 of the previous embodiment. As shown in FIG. 2, the primary camera unit 16' has a camera unit housing 20'. The primary camera unit 16' also has a power supply 32' and an audio mixer 26' for balancing the audio of external microphones 28' or internal microphones 30'. The primary camera unit router 18' is mounted within the primary camera unit 16' and is adapted to receive/transmit signals of audio/video data received from a pan-tilt-zoom (PTZ) camera 22' mounted within the camera unit housing 20'. The PTZ camera 22' may receive commands for rotating the camera in two degrees of freedom, known as panning and tilting of the camera, as well as lens magnification of the image or zooming. PTZ cameras are well known in the art. An exemplary camera is AXIS M5525-E PTZ/M5526-E PTZ Camera from AXIS Communications. The video output of the AXIS PTZ camera is H.264 (MPEG-4Part10/AVC) and H.265 (MPEG-HPart2/HEVC). This camera is also capable of live video streaming. The AXIS camera may also receive audio input from the external microphone 28' as well as transmitting audio output. In this embodiment, the PTZ camera 22' produces a video image of the patient simulator 12', instructors, and/or students while interacting with the patient simulator 12'. The audio/video from the primary camera unit 16' is transmitted by a wired or wireless connection to the remote processor 42'.

The primary camera unit 16' further includes a controller 24' for the PTZ camera 22'. The controller 24' includes a controller processor 25' that provides commands to the PTZ camera 22 with instructions to the PTZ camera 22 for controlling the operations of panning, tilting, and zooming actions taken by the PTZ camera 22 during a training session. The audio mixer 26' is electrically connected to external microphones 28' or internal microphones 30'. The power supply 32' is electrically connected to an external power source 34' or an internal battery 36'. The external power source 34' may be a standard electrical supply or Power over Ethernet (POE).

As in the previous embodiment, when the primary camera unit 16' receives a command, the controller 24' receives command instructions which are given to the PTZ camera 22' for performing a corresponding action by the PTZ camera 22'. For example, when the controller 24' is given a command to pan, tilt or zoom the PTZ camera 22', the PTZ camera 22' executes the corresponding action. Another command that the controller 24' may receive is a command to activate/deactivate the PTZ camera 22' operation as well as the microphones 28'/30'.

With the primary camera unit 16' acting as a central hub, secondary camera units 50' are connected to the primary camera unit 16' for transmitting audio/video in digital format to the remote processor 42' through the primary camera unit 16' and receiving commands from the remote processor 42' through the primary camera unit 16' regarding the functions of the secondary camera units 50'. Secondary camera units 50' are used to view the training session from different positions within the training area, thereby providing simultaneous views of the training session. Possible camera positions may provide an overall view of the scene, a zoomed-in view of the patient simulator 12', a zoomed-in view of an instrument tray, and a zoomed-in view of the attending physician/student or other views associated with the training session.

A screen capture unit 38' is wired or wirelessly coupled to the patient monitor 14'. This connection transmits a video signal from the patient monitor 14' as currently displayed. The screen capture unit 38' converts the video signal to a computer video file format. The screen capture unit 38' captures each video frame from the video signal and converts each video frame into sequenced frames of a video file. As in the previous embodiment, each frame of the video contains the image as displayed on the patient monitor 14'. A screen capture unit router 40' connects, through a wired or wireless connection, the screen capture unit 38' to the primary camera unit 16' for routing the video frames to the remote processor 42' through the primary camera unit 16'. Through this wired or wireless connection, the screen capture unit 38' transmits the digital video images containing the physiological data displayed on said patient monitor 14' to the remote processor 42' as either a single video file, segments of the training session, or live streaming of the training session. Typical screen capture units, such as screen capture unit 38' converts standard HDMI input up to 4096×2160 60 fps video with output to standard streaming protocols up to 16 Mbps, with support for H.264 (MPEG-4Part10/AVC) and H.265 (MPEG-HPart2/HEVC) video encoding.

In this embodiment, the physiologic data may be sent to the patient simulator 12' from the primary remote processor 42' or the local network 130. The patient simulator 12' simulates a prescribed medical procedure being demonstrated by the audio/video training system 10'.

As with the previous embodiment, the primary remote processor 42' has a remote processor display screen 46', and a remote processor router 44' for receiving the physiological data video which is passed through the primary camera unit 16' from the screen capture unit 38'. The remote processor router 44' of the primary remote processor 42' also receives the video images of the patient simulator 12' from the primary camera unit 16' and the secondary camera units 50'.

The remote processor display screen 46' is connected to the primary remote processor 42' for displaying the physiological data video from all of the video sources of the audio/video training system 10' including the patient monitor 14' via the screen capture unit 38' and the audio/video of the patient simulator 12' from the primary camera unit 16' and secondary camera units 50'.

As seen in the previous embodiment, a data storage unit 48' is coupled to the primary remote processor 42' for storing the physiological data used for the patient simulator 12', the video images of the patient simulator 12' via the primary camera unit 16' and the secondary camera units 50' and the physiological data video of the patient monitor 14' via the screen capture unit 38'. The data storage unit 48' shown in FIG. 2 is a cloud server, and may be other mass storage devices known in the art on location or remote to the audio/video learning system 10'.

Figure 5:
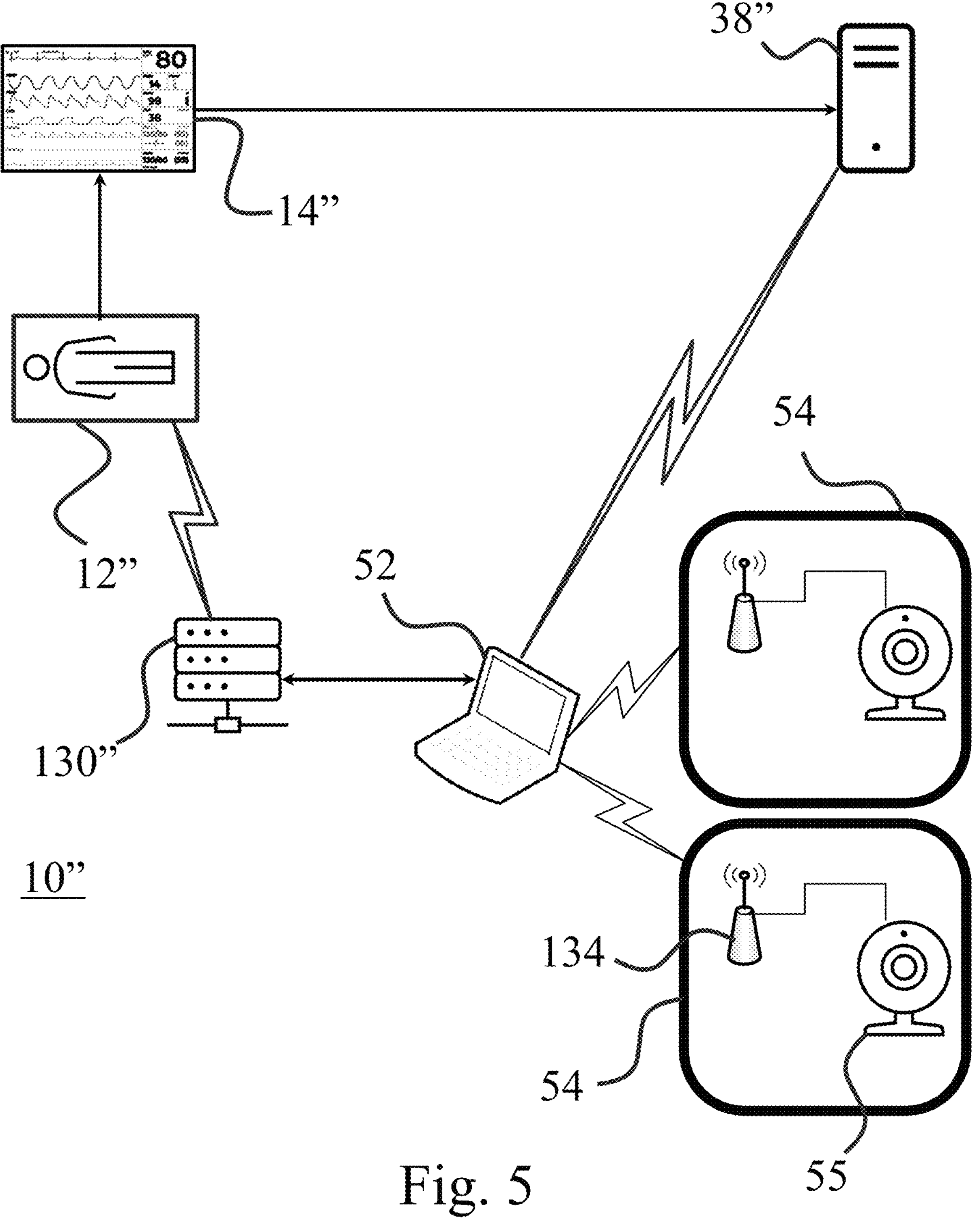
FIG. 5 is a depiction of a third embodiment of an audio/video training system.

In a further embodiment as seen in FIG. 5, the audio/video training system 10" includes a main wireless hub which may be a laptop 52 or controlling computer with wireless or wired connections to one or more independent camera units 54. The one or more independent camera units 54 include an independent camera unit router 134.

Laptop 52 connects to a patient simulator 12" through a local network 130". As with the previous embodiments, the patient simulator 12" connects to the patient monitor 14" which is connected to a screen capture unit 38". The screen capture unit 38" is connected to the laptop 52. All connections may be wired or wireless connections.

As shown in FIG. 5, each independent camera unit 54 includes an independent camera 55. Each independent camera unit 54 further includes additional individual components as previously described with the primary/secondary camera units in the previous embodiments.

Alternatively, the laptop 54 may connect directly to the patient simulator 12" as in the embodiment of audio/video training system 10 as shown in FIG. 1

Figure 6:
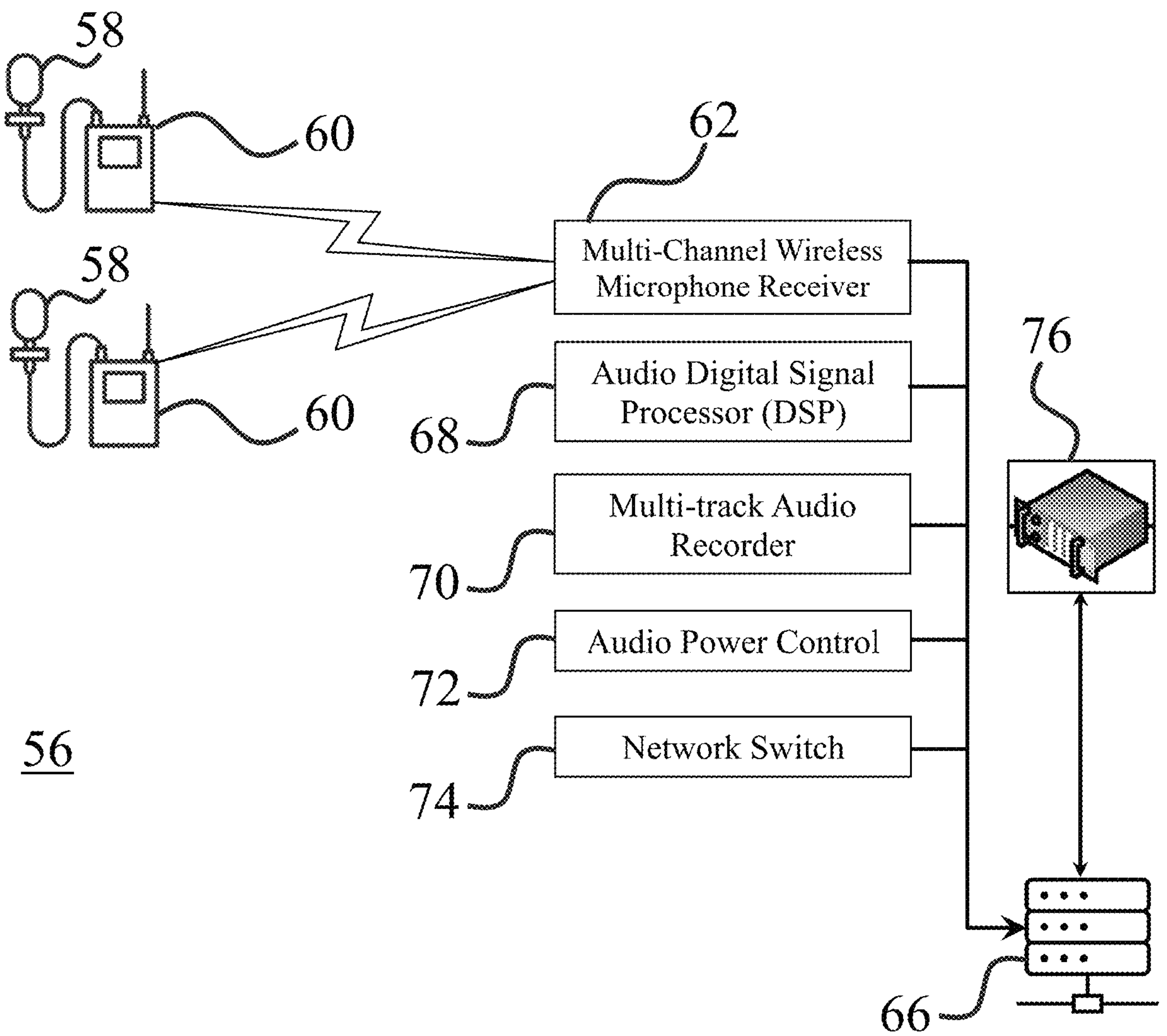
FIG. 6 shows a wireless audio system of a preferred embodiment.

As seen in FIG. 6, further embodiments of the audio/video training system 10/10'/10" may include an expanded wireless audio system 56. The expanded wireless audio system 56 includes throat microphones 58 connected to the audio/video training system 10/10'/10" through wireless microphone transmitters 60 and a multi-channel wireless microphone receiver 62 and functions as a wireless router receiver 64. The wireless microphone router 64 is connected to a main simulation network 66 through an Audio Digital Signal Processor (DSP) 68, a Multi-track Audio Recorder 70, audio power control 72, and a network switch 74. The Audio DSP 68 converts the analog audio signals to digital audio signals. An exemplary Audio DSP is the QSC Q-SYS Core 110*f*. The audio power control 72 is used to provide power to the wireless audio system 56. The network switch 74 routes the audio tracks to the main simulator network 66. The Wireless audio system 56 is also connected to a Network Time Protocol (NTP) Time Server 76, which is well known in the art. The NTP Time Server synchronizes the time of the entire audio/video training system 10. In addition to standard network performance, the NTP Time Server 76 allows for the embedding of a time code with each audio track and then time stamped digital audio tracks are recorded by way of the Multi-track Audio Recorder 70.

The main simulation network 66 connects to the patient simulator 12'/12" as the local network 130/130" in the previous embodiments and connected to the remaining elements of the audio/video teaching system 10'/10" in a similar manner. Alternatively, the main simulation network 66 may connect to the remote processor 42 of the audio/video teaching system 10.

Figure 7A:
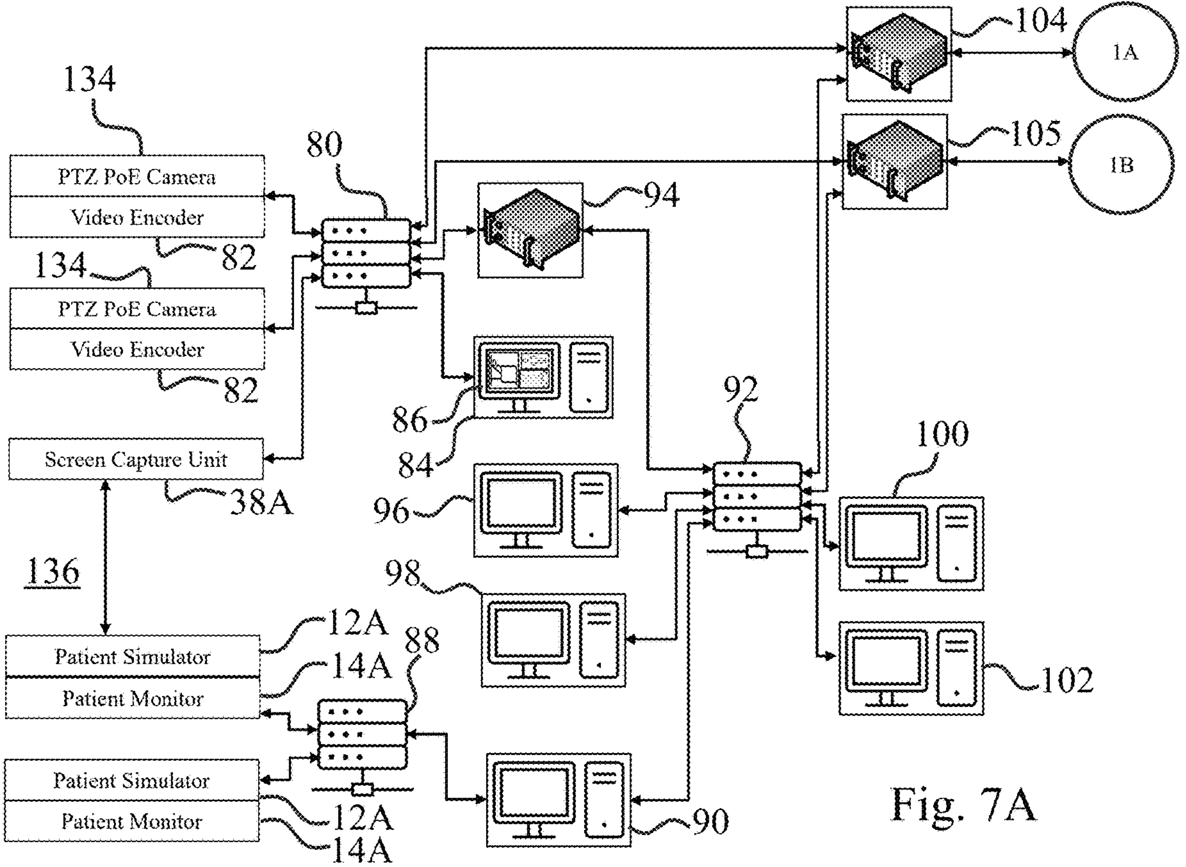
FIG. 7A and FIG. 7B combined are a depiction of a fourth embodiment of an audio/video training system.
Figure 7B:
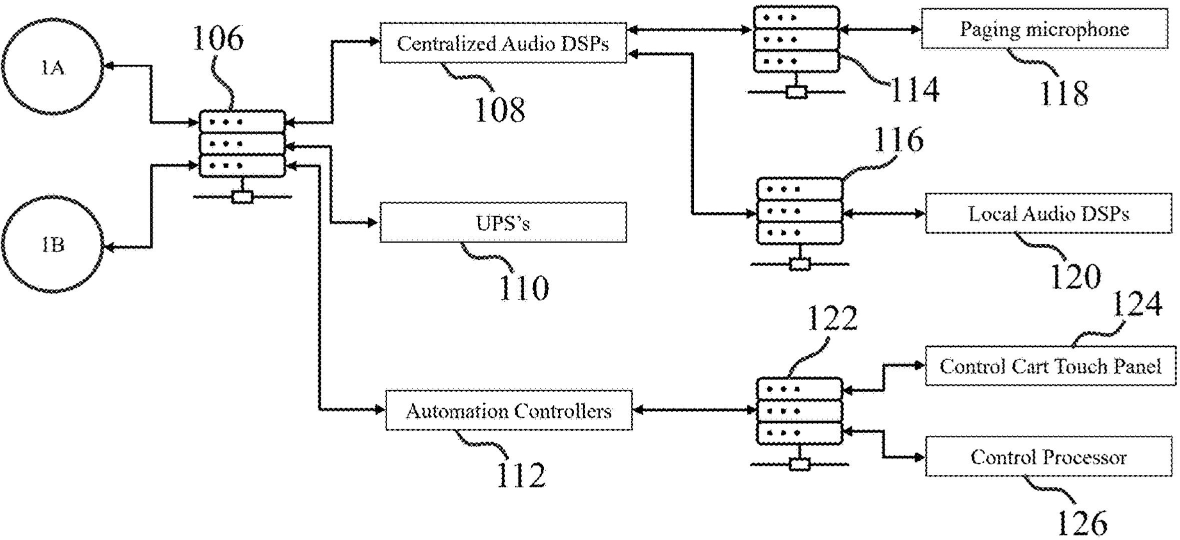

In another embodiment as seen in FIG. 7A and FIG. 7B, an audio/video training system 136 is depicted showing an expandable audio/video training system where the system may expand to include multiple training rooms/locations. Each location includes a Patient Simulator 12A, a Patient Monitor 14A, and associated PTZ cameras 134 and a screen capture unit 38A. In order to accomplish this, a multi-tiered subnetwork is utilized as seen in FIG. 7A and FIG. 7B.

As described in the previous embodiments, an exemplary patient simulator for patient simulator 12A is the Adult SimMan 3G produced by Laerdal Medical AS, a corporation of Norway, which is a full-body mannequin. Further patient simulators are available from Elevate Healthcare, INC., a corporation of Delaware located in Sarasota, Florida, which provides for a range of advanced patient simulators ranging from pediatric simulators to OB maternal simulators as well as surgery simulators.

As seen in FIG. 7A, an audio/video training system 136 includes multiple subnetworks and multiple training locations/rooms. Independent camera units 134 are connected to a Camera Video Local Area Network with Power over Ethernet (Camera VLAN PoE) 80. In this arrangement, communication may be made through a wired or wireless connection. Power may be provided to the independent camera units 134 through an Ethernet Connection. Power may also be provided through an internal battery or an external power source. An exemplary independent camera unit is the AXIS M5525-E PTZ/M5526-E PTZ Camera by AXIS Communications as described in the previous embodiments.

One or more Video Encoders 82 are connected to the VLAN POE 80. An exemplary video encoder is the VS-103E-3GSDI, HD H.264 Encoder by Marshall Electronics. This Video Encoder provides broadcast quality audio and video, based on IP network through LAN, ADSL/VDSL, and wireless LAN. The Marshall Video Encoder support H.264 and MJPEG video formats. Prior to transmission through the audio/video system 136, the Video Encoder 82 compresses the media data for efficient transmission.

A screen capture unit 38A is connected to a corresponding Patient Monitor 12A. The screen capture unit 38A performs the task of capturing the images displayed on the Patient Monitor 14A. The images displayed on the Patient Monitor 14A are physiologic data displayed as vital signs of the patient and can include the pulse rate, respiration rate, temperature, oxygen saturation (SpO2), carbon dioxide (CO2), blood pressure, and electrocardiography (ECG) readings. Such screen monitors are well known in the art, for example maybe the Philips IntelliVue MX700 bedside patient monitor providing a real-time view of the vital signs of patient simulators 12A.

A Multiplex Display PC 84 is connected to the Camera VLAN POE 80 for displaying all of the video signals from each of the one or more independent camera units 134 and the screen capture unit 38A on the display 86 of the Multiplex Display PC 84. The Multiplex Display PC 84 is capable of switching between each video signal or showing multiple video images side by side to monitor the functioning of the one or more independent camera units 134 and screen capture unit 38A. When a malfunctioning independent camera unit or Video Encoder is detected, the malfunction is addressed by the operator of the Multiplex Display PC 84.

A Mannequin Control Network 88 is connected to one or more Patient Simulators 12A and provides for controlling the one or more Patient Simulators 12A by one or more Mannequin Control PCs 90. The Mannequin Control PCs 90 are connected to the one or more Patient Simulators 12A through the Mannequin Control Network 88. Each of the one or more Mannequin Control PCs 90 may be configured to control a single Patent Simulator 12 or multiple Patient Simulators 12. In one configuration, one Mannequin Control PC Controls multiple Patient Simulators 12. In another configuration, each Patient Simulator 12 has a corresponding Mannequin Control PC 90.

The Mannequin Control PC 90 provides physiologic data parameters to the patient simulator 12, which is a specialized mannequin with the ability to simulate physiologic responses with the patient simulator 12.

The Mannequin Control PCs 90 are connected a Simulation VLAN 92 which serves as the main network for the users of the audio/video training network 136.

DVCS 94 are also connected between the Camera VLAN POE 80 and the Simulation VLAN 92. DVCS 94 may provide Dense Video Capturing or Deep Video Compression or combination thereof.

Also connected to the Simulation VLAN 92 are one or more Post Encounter PCs 96, one or more SP Checklist PCs 98, one or more Control Station PCs 100, and one or more Observation Station/Debrief PCs 102. The one or more Post Encounter PCs 96 provide data associate with the training session subsequent to the termination of the training session.

During operation of the audio/training system 136, each training session audio/visual recording may be bookmarked and have an event annotated during live recording or playback through the Observation Station/Debrief PCs 102. The annotated recordings are used during the review of the training session to assess the student's performance. The one or more SP Checklist PCs 98 are used to process an industry standard Specialized/Simulated Patient Checklist for each training session. Such checklists include questions related to the attending medical personnel's performance and interaction with the simulated patient.

For operation of the system, a Structured Query Language (SQL) Server 104 and an Internet Information Services (IIS) Server 105 are connected between the Camera VLAN POE 80, the Simulation VLAN 92, and a Control VLAN 106, as shown in FIG. 7B. SQL Servers are well known in the art of large database management and queries. IIS Servers are web servers well known in the art for providing access to websites, where in this application all traffic utilizes secured access.

As shown in FIG. 7B, connected to the Control VLAN 106 are Centralized Audio DSPs 108, UPS's 110, and Automation Controllers 112. The Centralized Audio DSPs 108 can be connected to audio networks such as a Dante VLAN 114 and/or an Audio Video Bridging (AVB) VLAN 116. The Dante VLAN 114 can provide uncompressed, multi-channel, low-latency digital audio over a standard Ethernet network using Layer 3 IP packets. The Dante VLAN 114 can receive audio input from a microphone such as a paging microphone 118 or other microphone. The AVB VLAN 116 can provide synchronization, low latency, and reliability for switched Ethernet networks. The AVB VLAN 116 synchronizes multiple inputs from one or more Local Audio DSPs 120. UPS's 110 provide backup power to the system, are well known in the art and commercially available.

Exemplary Centralized Audio DSPs 108 and Local Audio DSPs 120 are the Tesira SERVER by Biamp Systems LLC. The Tesira Server supports optional 32×32 CobraNet audio networking, and optional 64×64 Dante audio networking. The Tesira SERVER has system configuration and control via Ethernet or serial connection.

A Crestron VLAN 122 is connected to the Automation Controllers 112. The Automation Controllers 112 takes commands from a Control Cart Touch Panel 124 supported by a Control Processor 126. An exemplary control processor is the Crestron 4-Series Control System RMC4 by Crestron Electronics, Inc. This automation controller provides a secure, high-performance, control processor and interface for controlling and monitoring for a single display device, a small AV system, lighting and shading, climate control, security, and energy management.

The audio/video training system may provide training for many different scenarios. Each scenario is presented in a training session. These training sessions can include but not limited to Emergency Medicine, Health Systems, Medical & Nursing Schools, and Combat Medic Training. Emergency Medicine includes scenarios where the training system is deployed in ambulances or other scenarios where care is not in a standard medical facility. Health Systems include scenarios where the training system is deployed in an existing medical facility such as a hospital, urgent care facility, or nursing home to provide continuing education for existing medical personnel. Medical & Nursing Schools include scenarios where the training system is deployed in a specialized simulation environment in an educational institution for training out of the classroom to diversify patient care scenarios. Combat Medic Training includes scenarios where the training system is deployed in environments that replicate immersive battlefield conditions for treating warfighters. Such environments can include medical training on the battle front, training for medical personnel at an EVAC Station removed from the battle front, or at in-theater operating rooms located on forward bases near the battlefield.

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. An audio/video training system comprising:

a patient simulator connected to a patient monitor, said patient monitor for receiving and displaying patient physiological data;

at least a primary camera unit having a camera unit housing and a camera unit router mounted within said camera unit housing;

a pan-tilt-zoom (PTZ) camera mounted within said camera unit housing, said PTZ camera for capturing a video image of said patient simulator;

a screen capture unit coupled to said patient monitor and having a screen capture unit router, said screen capture unit in communication with said patient monitor for capturing a physiological data video of said physiological data displayed on said patient monitor, said physiological data video being routed to said primary camera unit;

a primary remote processor in communication with said patient simulator and having a remote processor router for receiving said physiological data video and said video image of said patient simulator from said primary camera unit;

a display screen connected to said primary remote processor for displaying said physiological data video and said video image of said patient simulator; and, a data storage unit coupled to said primary remote processor for storing said physiological data, said video image of said patient simulator and said physiological data video;

wherein said primary remote processor is in communication with said patient simulator through said primary camera unit for controlling physical parameters of said patient simulator responsive to said patient physiological data transmitted by said primary remote processor; said camera unit router of said primary camera unit provides connection and communication between at least said patient simulator, said camera, and said primary remote processor.

2. The audio/video training system as recited in claim 1 including a plurality of secondary camera units, each of said plurality of secondary camera units being in communication with said primary camera unit.

3. The audio/video training system as recited in claim 2, wherein each of said plurality of secondary camera units include a secondary camera unit housing, and a secondary PTZ camera mounted in each of said secondary camera unit housings.

4. The audio/video training system as recited in claim 3, wherein each of said secondary camera units transmits independently secondary video images of said patient simulator.

5. The audio/video training system as recited in claim 1, wherein said data storage unit is a cloud based storage unit for receiving said physiological data video and said video image of said patient simulator from said primary remote processor.

6. The audio/video training system as recited in claim 1, wherein data storage unit is a physical media storage medium for receiving said physiological data video and said video image of said patient simulator from said primary remote processor.

7. The audio/video training system as recited in claim 1 including a client computer network coupled to said primary camera unit, said data storage unit, and said patient simulator, said client computer network for receiving said patient physiological data, said physiological data video and said video image of said patient simulator.

8. The audio/video training system as recited in claim 7, wherein said client computer network is connected to said primary camera unit, said primary remote processor, and said patient simulator, said client computer network having a plurality of secondary remote processors and respective display screens.

9. The audio/video training system as recited in claim 8, wherein at least one secondary remote processor defines said physical parameters transmitted to said patient simulator.

10. The audio/video training system as recited in claim 7, wherein said data storage unit is a cloud based storage unit for receiving said physiological data video and said video image of said patient simulator from said primary remote processor.

11. The audio/video training system as recited in claim 7, wherein data storage unit is a physical media storage medium for receiving said physiological data video and said video image of said patient simulator from said primary remote processor.

12. An audio/video training system comprising:

a patient simulator connected to a patient monitor, said patient monitor for receiving and displaying patient physiological data;

at least a primary camera unit having a camera unit housing and a camera unit router mounted within said camera unit housing;

a pan-tilt-zoom (PTZ) camera mounted within said camera unit housing, said PTZ camera for capturing a video image of said patient simulator;

a screen capture unit coupled to said patient monitor and having a screen capture unit router, said screen capture unit in communication with said patient monitor for capturing a physiological data video of said physiological data displayed on said patient monitor;

a primary remote processor in communication with said patient simulator and having a remote processor router for receiving said physiological data video from said patient monitor and said video image of said patient simulator from said primary camera unit;

a display screen connected to said primary remote processor for displaying said physiological data video and said video image of said patient simulator; and, a data storage unit coupled to said primary remote processor for storing said physiological data, said video image of said patient simulator and said physiological data video;

wherein said camera unit router of said primary camera unit provides connection and communication between at least said screen capture unit, said camera, and said primary remote processor.

13. The audio/video training system as recited in claim 12, wherein said primary remote processor is in communication with said patient simulator through a local network for controlling physical parameters of said patient simulator responsive to said patient physiological data transmitted by said primary remote processor; and said camera unit router of said primary camera unit is in communication with said local network.

14. The audio/video training system as recited in claim 13 including a plurality of secondary camera units, each of said plurality of secondary camera units being in communication with said primary camera unit.

15. The audio/video training system as recited in claim 14, wherein each of said plurality of secondary camera units include a secondary camera unit housing, and a secondary PTZ camera mounted in each of said secondary camera unit housings.

16. The audio/video training system as recited in claim 15, wherein each of said secondary camera units transmits independently secondary video images of said patient simulator.

17. The audio/video training system as recited in claim 12, wherein said data storage unit is a cloud based storage unit for receiving said physiological data video and said video image of said patient simulator from said primary remote processor.

18. The audio/video training system as recited in claim 12, wherein data storage unit is a physical media storage medium for receiving said physiological data video and said video image of said patient simulator from said primary remote processor.

19. An audio/video training system comprising:

a patient simulator connected to a patient monitor, said patient monitor for receiving and displaying patient physiological data;

a primary camera unit having a camera unit housing and a camera unit router mounted within said camera unit housing, said camera unit router receiving said physiological data from said patient monitor;

a pan-tilt-zoom (PTZ) camera mounted within said camera unit housing, said PTZ camera for capturing a video image of said patient simulator;

a primary remote processor in communication with said patient simulator and having a remote processor router for receiving said physiological data video and said video image of said patient simulator from said camera unit router; and, a data storage unit coupled to said primary remote processor for storing said physiological data, said video image of said patient simulator and said physiological data video;

wherein said primary remote processor is in communication with said patient simulator through said primary camera unit for controlling physical parameters of said patient simulator responsive to said patient physiological data transmitted by said primary remote processor; said camera unit router of said primary camera unit provides connection and communication between at least said patient simulator, said camera, and said primary remote processor.

* * * * *